(12) United States Patent
Hultin et al.

(10) Patent No.: US 6,451,975 B1
(45) Date of Patent: *Sep. 17, 2002

(54) PROTEIN COMPOSITION AND PROCESS FOR ISOLATING A PROTEIN COMPOSITION FROM A MUSCLE SOURCE

(75) Inventors: Herbert O. Hultin, Rockport; Stephen D. Kelleher, Wakefield, both of MA (US)

(73) Assignee: Advanced Protein Technologies, Inc., Rockport, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 73 days.

This patent is subject to a terminal disclaimer.

(21) Appl. No.: 08/920,439

(22) Filed: Aug. 29, 1997

Related U.S. Application Data (63) Continuation-in-part of application No. 08/797,929, filed on Feb. 12, 1997.
(60) Provisional application No. 60/034,351, filed on Dec. 21, 1996.

(51) Int. Cl.[7] .................................................. C07K 1/14
(52) U.S. Cl. ...................................... 530/350; 530/412
(58) Field of Search .............................. 514/2; 530/350, 530/412, 344, 353

(56) References Cited

FOREIGN PATENT DOCUMENTS

GB        2048051        12/1980

OTHER PUBLICATIONS

"Sigma" catalog, 1995, p. 710.*
Chawla et al, Journal of food Science, vol. 61, No. 2, 1996, pp. 362–366 and 371.
Shahidi et al, Notes & Digests, Meat focus International–Oct., 1983, pp. 443–445.
Onodenalore et al, Journal of Aquatic food Product Technology, vol. 5(4), 1996, pp. 43–59.
Shahidi et al, Water Dispersions of Myfibrillar Proteins From Capelin (mallotus villosus), food Chemistry 53 (1995) 51–54.
Shahidi et al, solubilization and Termostability of Water Dispersions of Muscle Structures Proteins of Atlantic Herring (clupea horengus), J. Agric. food Chem., vol. 42, No. 7, 1994, pp. 1440–1446.
Venugopal et al, Thernostable Water Dispersions of Myofibrilla Protein from Atlantic Mackerl, (Scombler scombrus7, Journal of Food Science, vol. 59, No. 2, 1994,, pp. 265–276.
Cuq et al, Edible Packaging Films bsed in Fish Myofibrillar Proteins; Formulation and Functional Properties, Journal of Food Science, vol. 60, No. 6, 1995, pp. 1369–1374.
Wilmon W. Meinke, Muhammad A. Rahman and Karl F, Mattil, Journal of Food Science, vol. 37, (1972) pp. 195–198, Some Factors Influencing The Production Of Protein Isolates From Whole Fish.
Wilmon W. Meinke and Karl F. Mattil, Journal of Food Science, vol. 38, (1973), pp. 864–866, Autoysis As A Factor In The Production Of Isolates From Whole Fish.

* cited by examiner

Primary Examiner—Michael Borin (57) ABSTRACT

A process is provided for isolating a protein component of animal muscle tissue by mixing a particulate form of the tissue with an acidic aqueous liquid having a pH below about 3.5 to produce a protein rich solution substantially free of myofibrils and sarcomere tissue structure. The protein rich aqueous solution can be treated to effect protein precipitation, followed by protein recovery.

17 Claims, 4 Drawing Sheets

PROTEIN COMPOSITION AND PROCESS FOR ISOLATING A PROTEIN COMPOSITION FROM A MUSCLE SOURCE

REFERENCE TO RELATED APPLICATIONS

This application is a continuation-in-part of application Ser. No. 08/797,929 filed Feb. 12, 1997, which in turn, is a continuation-in-part of provisional application Serial No. 60/034,351, filed Dec. 21, 1996.

This invention was made with government support under Grant NA90AA-D-SG24 awarded by the U.S. Department of Commerce (NOAA). The government has certain rights in the invention.

BACKGROUND OF THE INVENTION

1. Field of the Invention

This invention relates to a process for recovering protein from an animal muscle source with improved functional properties and to the protein product so-obtained. More particularly, this invention relates to a process for recovering muscle proteins with improved functional properties from an animal source and the protein product so-obtained.

2. Description of Prior Art

Presently, there is an interest in expanding the use of muscle proteins as food because of their functional and nutritional properties. Better use of these materials would be particularly important with aged or frozen raw materials which are less valuable because they have lost protein functionality. It is presently believed that the muscle tissue utilized as the feed in present processes must be fresh rather than frozen or aged. It is common commercial practice to process freshly caught fish at sea on board ship rather than subject the fish to the time of transportation or the freezing necessary to effect processing on land. Ageing or freezing of fish lowers the functional qualities of the tissue proteins. Protein functionalities of most concern to food scientists are solubility, water holding capacity, gelation, fat binding ability, foam stabilization and emulsification properties.

Protein concentrates from muscle tissue, especially fish, have been made by hydrolysis. This approach has improved some functional properties, particularly solubility, which has allowed its use in prepared soups. However, this approach also destroys other functional properties such as gelling ability.

One process that has had some success in stabilizing protein foods has been the process for producing "surimi". This conventional process has been used primarily for fish, although there have been some attempts to produce a surimi-like product from other raw materials such as mechanically deboned poultry mince. In producing surimi, the fresh muscle is ground and washed with a variable amount of water a variable number of times. This is determined by the location of the plant and the product that is desired from the particular species. Water may be used in a ratio as low as about 2 parts water to one part fish up to about 5 parts water per 1 part fish; typically about 3 parts water are used per 1 part fish. The number of washes can vary, generally, from 2 to 5, again depending on the raw material, the product desired, and water availability. Twenty to thirty per cent of the fish muscle proteins are solubilized when the ground muscle is washed with water. These soluble proteins, known as sarcoplasmic proteins, are generally not recovered from the wash water of the process. This loss is undesirable since sarcoplasmic proteins are useful as food. The washed minced product containing the protein in solid form then is used to make protein gels. Originally, this was used to produce "kamaboko" in Japan. Kamaboko is a popular fish sausage in which the washed minced fish is heated until it gels. It is presently believed that it is necessary to add cryprotectants to the washed, minced fish before freezing to prevent protein denaturation. A typical cryoprotectant mixture comprises about 4% sucrose, about 4% sorbitol and about 0.2% sodium tripolyphosphate. These components retard the denaturation of the protein during freezing, frozen storage and thawing.

It has been proposed by Cuq et al, Journal of Food Science, pgs. 1369–1374 (1995) to provide edible packaging film based upon fish myofibrillar proteins. In the process for making the films, the protein of water-washed fish mince is solubilized in an aqueous acetic acid solution at pH 3.0 to a final concentration of 2% protein. No attempt was made in this work to re-adjust the pH values of the acidified proteins to re-establish the functional properties attained at pH values above about 5.5. In addition, the use of acetic acid imparts a strong odor to the material which would severely limit its use in a food product.

It also has been proposed by Shahidi and Onodenalore, Food Chemistry, 53 (1995) 51–54 to subject deboned, whole capelin to washing in water followed by washing in 0.5% sodium chloride, followed by washing in sodium bicarbonate. The series of washes, including that using sodium bicarbonate, would remove greater than 50% of the muscle proteins. Essentially all of the sarcoplasmic proteins would be removed. Final residue was further washed to remove residual bicarbonate. The washed meat was then suspended in cold water and heated at 70° C. for 15 min. This heat treatment is sufficient to "cook" the fish proteins, thus denaturing them and reducing or eliminating their functional properties. No attempt was made to restore proteins to improve the functional properties of the capelin proteins.

Shahidi and Venugopal, Journal of Agricultural and Food Chemistry 42 (1994) 1440–1448 disclose a process for subjecting Atlantic herring to washing in water followed by washing with aqueous sodium bicarbonate. Again, this process will remove greater than 50% of the muscle proteins, including the sarcoplasmic proteins. The washed meat was homogenized and the pH varied between 3.5 and 4.0 with acetic acid. In addition, there is an unacceptable odor problem with the volatile acetic acid.

Venugopal and Shahidi, Journal of Food Science, 59, 2 (1994) 265–268, 276 also disclose a similar process for treating minced Atlantic mackerel. The material is washed sequentially with water, bicarbonate solution and again water. The pH is brought to pH 3.5 with acetic acid after homogenization. The proteins were precipitated at pH values greater than 4 on heating the material to 100° C. for 15 min. It is disclosed that "dissolution of structural proteins of fish muscle requires extractants with an ionic strength >0.3".

Shahidi and Venugopal, Meat Focus International, October 1993, pgs 443–445 disclose a process for forming homogenized herring, mackerel dispersions or capelin dispersions in aqueous liquids having a pH as low as about 3.0. It is reported that acetic acid reduces the viscosity of herring dispersions, increases viscosity of mackerel to form a gel and precipitates capelin. All of these preparations were initially washed with water and sodium bicarbonate, which would remove a substantial proportion of the protein, including the sarcoplasmic proteins.

Chawla et al, Journal of Food science, Vol. 61, No.2, pgs 362–366, 1996 discloses a process for treating minced threadfin bream muscle after it has been washed twice with water and recovered by filtration. The minced fish product is mixed with tartaric, lactic, acetic or citric acid, is allowed to set and then is heated in a boiling water bath for twenty minutes and then cooled to form a gel. This heat treatment is sufficient to denature the proteins. The washing steps undesirably remove soluble sarcoplasmic proteins from the mince. It is also disclosed that unwashed mince failed to provide the desired gel forming property of surimi.

Onodenalore et al, Journal of Aquatic Food Products Technology, Vol. 5(4), pages 43–59 discloses that minced shark muscle is a source of acidified protein compositions. The minced product is washed sequentially with aqueous sodium chloride, aqueous sodium bicarbonate and then water to remove metabolic substances. This washing effects undesirable removal of sarcoplasmic proteins. The minced product is recovered by filtration. The minced product then is acidified to pH 3.5 with acetic acid, heated in a boiling water bath, cooled and centrifuged to recover a supernatant. The supernatant pH was adjusted to a pH 4–10 using NaOH, heated in a boiling water bath, cooked and centrifuged to recover a second supernatant. Heating the protein dispersion comprising the minced product resulted in 87–94% of the protein remaining in solution while heating of the unacidified protein dispersion resulted in protein coagulation. However, the heating causes protein denaturation.

Accordingly, it would be desirable to provide a process for recovering a high proportion of available muscle protein from an animal source including a frozen or aged animal source, rather than requiring a fresh muscle tissue source. It would also be desirable to provide such a process, which permits the use of muscle protein sources which are presently under-utilized as a food source such as frozen or aged fish. Furthermore, it would be desirable to provide such a process which recovers substantially all of the protein content of the process feed material. In addition, it would be desirable to provide such a process which produces a stable, functional, protein product which is particularly useful for human consumption. Such a process would permit its operation at will rather than require initiation of the process very shortly after the animal source is killed so that processing can be extended over a desired time schedule.

BRIEF DESCRIPTION OF THE INVENTION

This invention is based upon our newly discovered properties of the myofibrillar and sarcoplasmic proteins of muscle tissue which permit their processing at low pH, below about 3.5. Muscle tissue (fish or meat) is disrupted to form particles, such as by being ground or homogenized with enough water and at a pH to solubilize a major proportion, preferably substantially all of the available protein. Solubilization is effected at a low pH below about 3.5, but not so low as to effect substantial destruction of proteins, preferably between about 2.5 and about 3.5. During the solubilization step, the myofibril and sarcomere tissue structure is substantially completely converted to solubilized protein so that the final product obtained as described below is substantially free of the myofibril and sarcomere tissue structure. This process differs from the conventional process for making surimi in that major myofibrillar proteins are never solubilized in the conventional process. In the conventional process, of making surimi myofibrillar proteins are simply washed in water or in water that has been made slightly alkaline to remove water-soluble materials that lead to loss of quality of the product. Unfortunately, this conventional process also removes water-soluble sarcoplasmic proteins.

In an optional embodiment of this invention, the disrupted muscle issue can be mixed with an aqueous solution to give a pH typically between about 5.0 and about 5.5 to provide a suspension of muscle particles which can be more easily treated to solubilize proteins in the subsequent low pH treatment step to produce a solution having a sufficient low viscosity, i.e, a non-gel, so that it can be easily processed. By conducting this optional preliminary step at pH between about 5.0 and about 5.5, a homogeneous suspension is obtained wherein the protein does not imbibe excessive concentration of water. Thus, reduced volumes of water are processed which must be treated to effect the desired lower pH in the subsequent solubilization step.

The solubilized protein material from the low pH treatment step, then is treated to precipitate the proteins such as by raising its pH to between about 5.0 and about 5.5, addition of salt, the combination of salt addition and increase in pH, the use of a coprecipitant such as a polysaccharide polymer or the like to recover an insoluble protein product containing myofibrillar proteins and a significant proportion of the sarcoplasmic protein of the original muscle tissue proteins in the original muscle tissue process feed. "The protein product can contain membrane protein present in the original animal tissue process feed." Also, as set forth above, the precipitated protein is substantially free of myofibril and sarcomere tissue structure. Myofibrils and sarcomere tissue comprise strands of tissue or portions of tissue strand structure which can be viewed under a microscope. Myofibrils and sarcomere are formed primarily of proteins.

In an alternative process of this invention, the muscle tissue can be washed to obtain an aqueous solution of sarcoplasmic protein. This solution is treated at low pH as set forth above and then precipitated as set forth above in the presence of myofibrillar protein.

In an alternative process, this precipitation step need not be conducted to recover the protein product. The protein product can be treated directly without raising its pH such as by precipitation with a salt, polymer or the like and can be spray dried to be used, for example, in acidic foods. Alternatively, the low pH protein-rich solution can be treated to improve its functional properties, such as with an acidic proteolytic enzyme composition or by fractionating the protein.

The precipitated protein composition recovered at the higher pH condition can be further treated to produce a food product. Such further treatment can include lyophilization, freezing with or without an added cryoprotectant composition and with or without raising its pH or gelation by raising its pH.

DESCRIPTION OF SPECIFIC EMBODIMENTS

In accordance with this invention, animal muscle is disrupted to form particles such as by grinding, homogenization or the like. As an optional preliminary step, the animal muscle tissue source of protein is ground and mixed with an aqueous liquid at a pH below about 3.5 and at a ratio of volume of aqueous liquid to weight of tissue to form an aqueous composition which does not have an undesirably high viscosity which renders recovery of the protein difficult. As a result of this low pH condition, the protein solution is rendered substantially free of myofibrils and sarcomeres. The animal muscle source can be fresh, aged or frozen. Typically, the ratio of volume of aqueous liquid to weight of tissue is greater than about 7:1, preferably greater than about 9:1. Lower ratios of volume of aqueous liquid to tissue weight can be utilized, depending upon the species source of muscle tissue when the animal muscle source exhibits a reduced tendency to cause gelation at the lower ratios. By utilizing these conditions of pH and ratio of aqueous liquid volume to tissue weight, the protein component of the tissue is dissolved in the aqueous liquid while avoiding gelation of the composition in this step. The pH should not be so low as to destroy a substantial portion of the protein over the time period the protein is in solution i.e., below about pH 1.0. Protein denaturation and protein hydrolysis also are a function of temperature and time in solution with increased temperature and increased time in solution promoting protein denaturation and protein hydrolysis. Thus, it is desirable to reduce solution temperature and the time protein is in solution, particularly when a lower pH of the protein solution is attained, for example about 2.0 or below. The aqueous liquid composition also may contain components which do not degrade or hydrolyze the proteins in solution such as salts, for example, sodium chloride or the like. The ionic strength of the solution should be maintained below about 200 mM to avoid protein precipitation when it is not desired.

In an optional preliminary step, the disrupted animal muscle tissue is mixed with an acidic aqueous solution to a pH of about 5.0 to about 5.5. Thereafter, the pH of the mixture is reduced with acid as described above in order to solubilize the proteins. It has been found that this preliminary mixing step provides protein solutions of reduced viscosity in the low pH treatment step described above and therefore, promotes ease of processing to recover the protein.

At this point, the solubilized composition optionally can be fractionated, in order to recover a particular desired protein fraction or derived product fraction if desired by size exclusion chromatography or other techniques based on properties of the proteins, other than molecular size, since the materials are solubilized in a solution of low viscosity. Alternatively, the protein in solution can be dehydrated, for example, by spray drying, to produce a functional protein for use in acid foods such as salad dressing, mayonnaise, gels or as a nutrient supplement to fruit juices, sodas, or the like. This point of the process provides a convenient time to treat the dissolved proteins with acidic proteolytic enzymes, if desired to modify the proteins to improve their functional properties as desired. Some limited proteolysis may occur at the low pH. This proteolysis depends on time, temperature, and the specific pH value.

The recovered protein-rich solution/colloidal suspension can then be adjusted to a pH at which essentially all of the proteins precipitate, such as between about 5.0 and about 6.5. This pH will vary depending upon the animal source of the protein and is generally between about 5.0 and about 5.5, more usually between about 5.3 and about 5.5. The protein can be recovered again, such as by centrifugation or with a polymeric precipitant, e.g., a polysaccharide or combination thereof or the like. Not only are all of the myofibrillar and cytoskeletal proteins recovered, but the soluble sarcoplasmic protein fraction which has been previously solubilized at the reduced pH below about 3.5, but not separately recovered is also precipitated by raising the pH to between about 5.0 and about 5.5. This recovery of the sarcoplasmic proteins is not observed when the sample is directly reduced in pH to about 5.5 and centrifuged. It is necessary to attain the low pH condition and then return to the pH condition where protein precipitation is effected to prevent this protein loss. When the low pH condition is not preliminarily obtained, the protein loss is generally between about 20 and about 30% of the original process feed protein, primarily due to loss of sarcoplasmic protein. The precipitated protein is separated from the aqueous liquid compositions which contain soluble impurities such as low molecular weight metabolites, sugars, phosphates and/or nucleotides. Alternatively, protein precipitation can be attained with precipitating polymers such as polysaccharides, charged polymers, marine hydrocolloids including alginates or carrageenan or the like either alone or in combination with centrifugation. In addition, as set forth above, precipitation can be effected by addition of salt or by the combination of pH control and addition of salt. While applicants do not intend to be bound by a particular theory to support unproved protein recovery, this enhanced recovery may be due to either molecular changes in the sarcoplasmic proteins whence they become insoluble at that pH, or they may bind more readily to the myofibrillar and cytoskeletal proteins due to molecular changes in the latter proteins. Alternatively, it may be that the opening up of the myofibrillar and cytoskeletal proteins provide more binding sites for the sarcoplasmic proteins.

In any event, applicants have found that treating the protein solution at the low pH condition set forth above improves the functionality of the protein. This observed improvement permits the use of aged or frozen muscle tissue as a starting material in the process of this invention. In addition, fresh muscle tissue can be used as a starting material in the process of this invention.

The rate at which the pH of optimal precipitation is reached can have an effect on the nature of the association of the collected proteins. Rapid change in pH by direct addition of base can produce an aggregated mass of proteins whereas a slow change in pH, for example, that achieved by dialysis, can allow proteins to specifically associate with the proteins with which they are normally associated in the fibrils.

Any acid that does not undesirably contaminate the final product can be used to lower the pH such as organic acids including citric acid, malic acid, tartaric acid or the like or mineral acids such as hydrochloric acid or sulfuric acid or the like or mixtures thereof. Citric acid which has favorable pKa values is a preferred acid for the process. Sufficient citric acid provides adequate buffering capacity at pH 3 and pH 5.5 and then hydrochloric acid can be used to reduce the pH to the desired point. Acids that have significant volatility which impart undesirable odor such as acetic acid or butyric acid are undesirable. Likewise, any of several bases can be used to raise the pH. It is preferred to add a polyphosphate since this also functions as an antioxidant and improves the functional properties of the muscle proteins.

The precipitated protein optionally can be treated in many ways. For example, its pH may be raised to neutrality, cryoprotectants added, and frozen to make a typical "surimi". Surimis prepared by this process have excellent functional quality. The "true strain" (a measure of protein quality) has been as high as 2.8 for cod and 2.6 for light muscle as animal protein sources. The product has reduced lipid. The precipitated protein can be dehydrated after the addition of agents currently used in surimi processing such as starches to prevent aggregation of the protein, such as, but not limited to, negatively charged compounds for use in the production of products such as gels, emulsifiers and viscosity developers. The precipitated protein can also be re-acidified to pH of from about 2.5 to about 3.5 using less liquid volume than it previously contained to concentrate the protein prior to dehydration. This provides energy savings for the dehydration step. In addition the recovered protein compositions can be fractionated to recover constituent proteins. The resultant product is useful as an ingredient in products such as those described above.

When utilizing animal muscle tissue which is relatively high in fat, oil and/or lipids, the fat, oil and/or lipid can remain with the precipitated protein which may render the protein-rich product susceptible to degradation, primarily by oxidation. Accordingly, the protein-rich product can be treated such as by being stored in a vacuum, stored frozen, by adding an antioxidant thereto such as isoascorbic acid, ascorbic acid, erythorbic acid, propyl gallate, tocopherols or the like.

This invention improves upon the prior art in that:

1. Aged or frozen muscle tissue can be used as a feed composition which permits scheduling of the process to accommodate a desired time period. It is not necessary in the process of this invention to require very fresh product as a starting material. The ability of the process of this invention to use non-fresh and even frozen fish is very important for a fishing fleet catching the fish and permits use of shore-based plants to effect the process of this invention since it eliminates the requirement for using fresh fish fillet sources now required by presently available processes.

2. The process of this invention provides for increased yield of protein. Greater than about 90% of protein typically are obtained from light muscle tissues with the process of this invention, whereas prior art similar processes provide less than about 60% protein recovery. In some cases, the protein yields obtained with the present invention are as great as about 95%.

3. The improved yield of protein as product means that there is less protein to recover/remove in the waste water, so that by-product pollution is decreased.

4. The color of the product of this invention is much improved over the color of prior art products. The color of surimi now made from pelagic fish with presently available processes is typically grayish in color with a high Hunter "b" value. A white color as good or better than the best grade of surimi made from lean white-fleshed fish from presently available processes is obtained with the process of the present invention from the light muscle of mackerel as the starting animal protein source. As a process feed material, mackerel light muscle from fish stored between 2 and 3 days on ice typically provides a product of this invention having "L", "a", "b" values of 78.4, −0.89 and 2.0 with a whiteness index of 78.3 or better.

5. In prior art processes, a majority of the muscle proteins are insoluble throughout the process. The process of this invention solubilizes approximately 98% of the muscle proteins. This reduces process time, promotes process ease of control and renders the process adaptable to continuous processing.

6. An obvious use for the process of this invention is to utilize materials which are not available now as human foods because of their instability and unfavorable sensory qualities. Stability can be improved with the process of this invention when utilizing stability enhancing compositions such as antioxidants or the like. An example of the use in the present invention are the small pelagic species of fish such as herring, mackerel, menhaden, capelin, anchovies, sardines, or the like as starting materials, which presently are either underutilized or are used primarily as industrial fish and not for human consumption. Approximately one half the fish presently caught in the world are not used for human food. A process that produces an acceptable stable protein concentrate for human consumption constitutes an important value-added use of this material and an important contribution to world nutrition. For example, the estimated annual sustainable yield of mackerel, menhaden and herring available off the Atlantic coast of the United States is as high as 5 billion pounds. The process of this invention also can be used to process flesh that is recovered from farmed fish after the fillets have been removed. This material currently is not used for human food. Representative suitable starting sources of animal protein for the process of this invention include fish fillets, deheaded and gutted fish, including pelagic fish, crustacea, e.g., krill, mollusc, e.g. squid or chicken, beef, lamb, sheep or the like. For example, a large quantity of mechanically deboned chicken meat presently is produced from the skeletons of the birds after chicken parts are removed for retail sale. The process of the present invention can utilize such chicken parts to produce protein rich product useful for human enterprise. Other under-utilized muscle sources adaptable to the process of this invention include Antarctic krill, which is available in large quantities but is difficult to convert to human food because of its small size. The process also is capable of utilizing most unstable or low value muscle tissue.

A specific example of the process of the present invention comprises a plurality of steps, including optional steps. In a first step, an animal protein source is ground to produce a composition of particles having a high surface area which promotes subsequent processing. In an optional second step, the ground protein source can be washed with water, typically with about 1 to 9 or more volumes of water based on the weight of ground muscle source. When utilizing the optional washing step, the liquid soluble fraction is separated from the insoluble fraction such as by centrifugation with the insoluble fraction being processed further as described below. The liquid fraction contains solubilized proeins and lipids. while this washing step removes a portion of undesirable lipids, it also undesirably removes proteins, particularly sarcoplasmic proteins. The recovered protein-rich water fraction then can be introduced downstream into the process for further processing the insoluble fraction from the washing step so that the proteins in the wash liquid soluble fraction can be recovered. The ground animal protein source is pulverized with water which also can contain acid, such as citric acid to obtain a pH such as from about 5.3 to about 5.5 to produce small particles which promote their solubilization in a subsequent step wherein the pH of the composition is reduced. When conducting this step at a pH between about 5.3 and about 5.5, undesirable swelling of the composition is avoided or minimized.

The composition of pulverized protein-rich composition then is mixed with an acid composition to reduce the pH below about 3.5 but not so low as to significantly destroy the protein, such as about 2.0 or even as low as about 1.0. Suitable acids are those which do not significantly destroy the protein and do not render the final product toxic. Representative suitable acids include hydrochloric acid, sulfuric acid or the like. This process step conducted at low pH contrasts with the prior art process conditions at a high pH close to neutral pH. The resulting composition comprises a low viscosity solution in which substantially all of the protein from the animal protein source is soluble and is substantially free of myofibrils and sarcomere tissue structure.

The low pH solution then can be fractionated, if desired to separate solids from the aqueous fraction or fractions, such as by filtration or decantation to remove solids, such as bone, when present. The protein-rich aqueous component is recovered for further processing as described below.

The protein in the low viscosity solution then is treated to precipitate the proteins. The protein in solution then is precipitated such as by raising the solution pH above about 5.0, preferably to about 5.5. Alternatively, salt or a precipitating polymer can be used to effect precipitation. When the above-described washing step of the initially ground tissue is eliminated, the water-soluble protein, including the sarcoplasmic protein from the ground tissue is recovered in this step. Typically, the sarcoplasmic protein comprises about 20–30% of the total protein in the original tissue. The processes of the prior art do not recover this protein. While the initial washing step removes this protein from the tissue being processed, it can be recovered in the process of this invention as described above. Even when this initial washing step is included in the process of this invention and the sarcoplasmic protein is recovered separately, the process of this invention provides substantial advantages since it is capable of processing animal protein sources, including high fat and high oil sources which can not be economically processed to produce food for human consumption with presently available processes.

The product of this invention differs from the products of the prior art in that the precipitated solid and liquid solution products of this invention are substantially free of myofibrils and sarcomere tissue. In contrast, the products of the prior art processes for producing surimi contain myofibrils and sarcomeres. In addition, the product of this invention which comprises primarily myofibrillar protein, also can contain significant amounts of sarcoplasmic protein. The sarcoplasmic protein in the protein product typically comprises above about 8%, preferably above about 15% and most preferably above about 18% sarcoplasmic proteins by weight, up to about 30% by weight based on the total weight of protein in the product.

The precipitated product can be used directly as a food source. Alternatively, the precipitated product can be further treated such as by removing a portion of the water in the product, by lyophilization, freezing, or heat drying. The resultant product can be in the form of a solution, a gel or a dry particulate product. The product is useful as a food grade composition for human consump- and has a wide variety of uses. The product can be used, for example, to form the major portion of artificial crab meat or as a food additive such as a binding agent or the like. In addition, the product can be used as an emulsifier, as a thickening agent, as a foaming agent, as a gelling agent, as a water binding agent or the like, particularly in food products.

Figure 1:
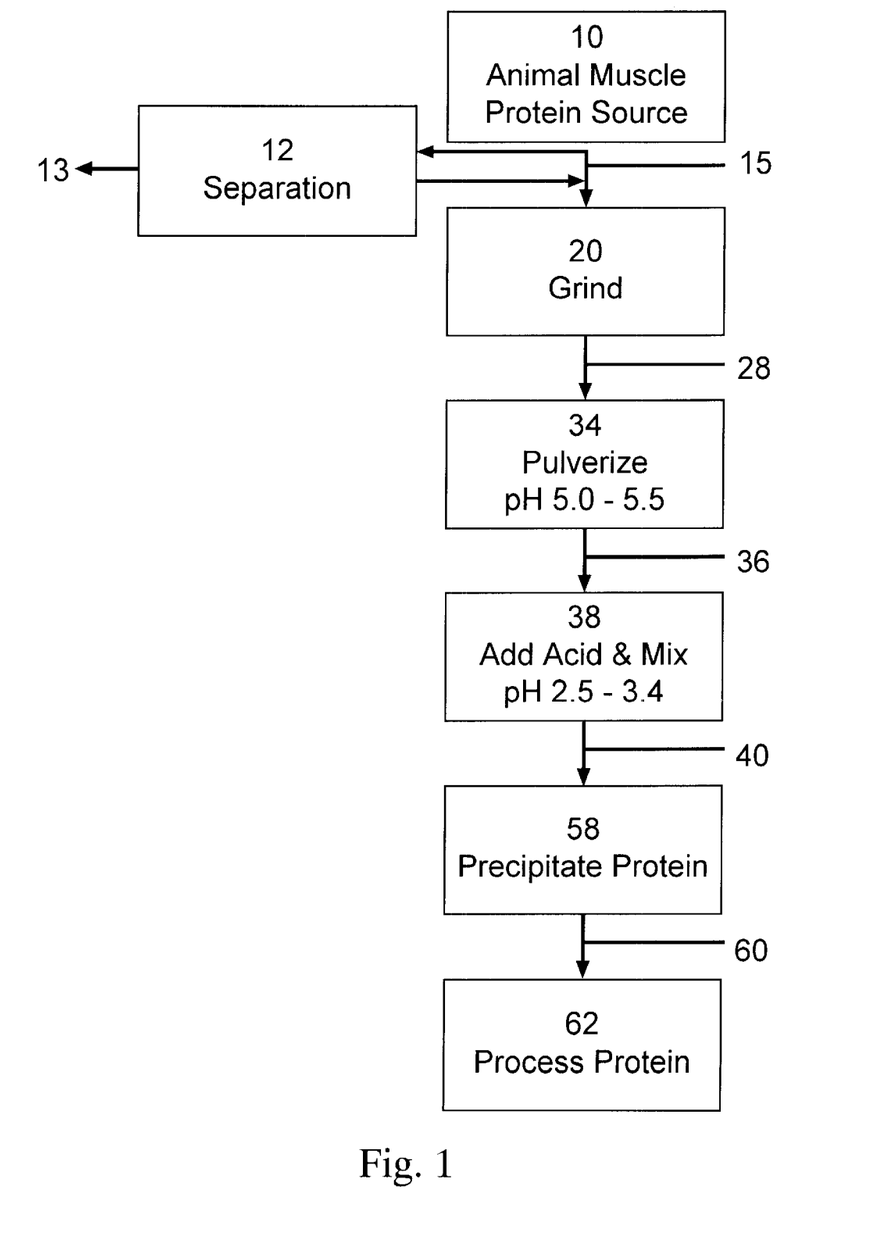
FIG. 1 is a general schematic diagram illustrating the process of this invention.

FIG. 1 illustrates the general process of this invention including some optional process steps. In a first step an animal muscle protein source 10 can optionally be introduced into a conventional cold press or centrifugation or the like, step 12 wherein the feed, such as ground fish, is subjected to a pressure, to separate an aqueous liquid containing fats and oils 13 from solid tissue 15. The solid animal tissue 15 then is ground in step 20 to increase its surface area. Alternatively, steps 12 and 20 can be reversed. The ground tissue 28 is pulverized and its pH reduced with an aqueous acidic solution to about 5.0 to about 5.5 in step 34. The aqueous composition 36 then is mixed with acid in step 38 to reduce its pH to between about 3.0 and about 3.5. The aqueous rich, protein containing streams can be added to step 38 for processing therein. The resultant low pH protein rich fraction 40, directed to step 58 wherein its pH is raised, such as to between about 5.0 about 6.5 to effect precipitation of substantially all protein in solution. Optionally, stream 56 can be treated such as by salt precipitation, precipitation with a precipitating polymer or combinations thereof or the like, rather than being precipitated in step 58. The precipitated protein 60 can be further processed in step 62 such as by lyophilization, freezing in the presence of a cryoprotectant or by being gelled.

The following example illustrates the present invention and are not intended to limit the same.

EXAMPLE 1

This example provides a comparison of the process of this invention to a presently used process of the prior art.

Figure 2:
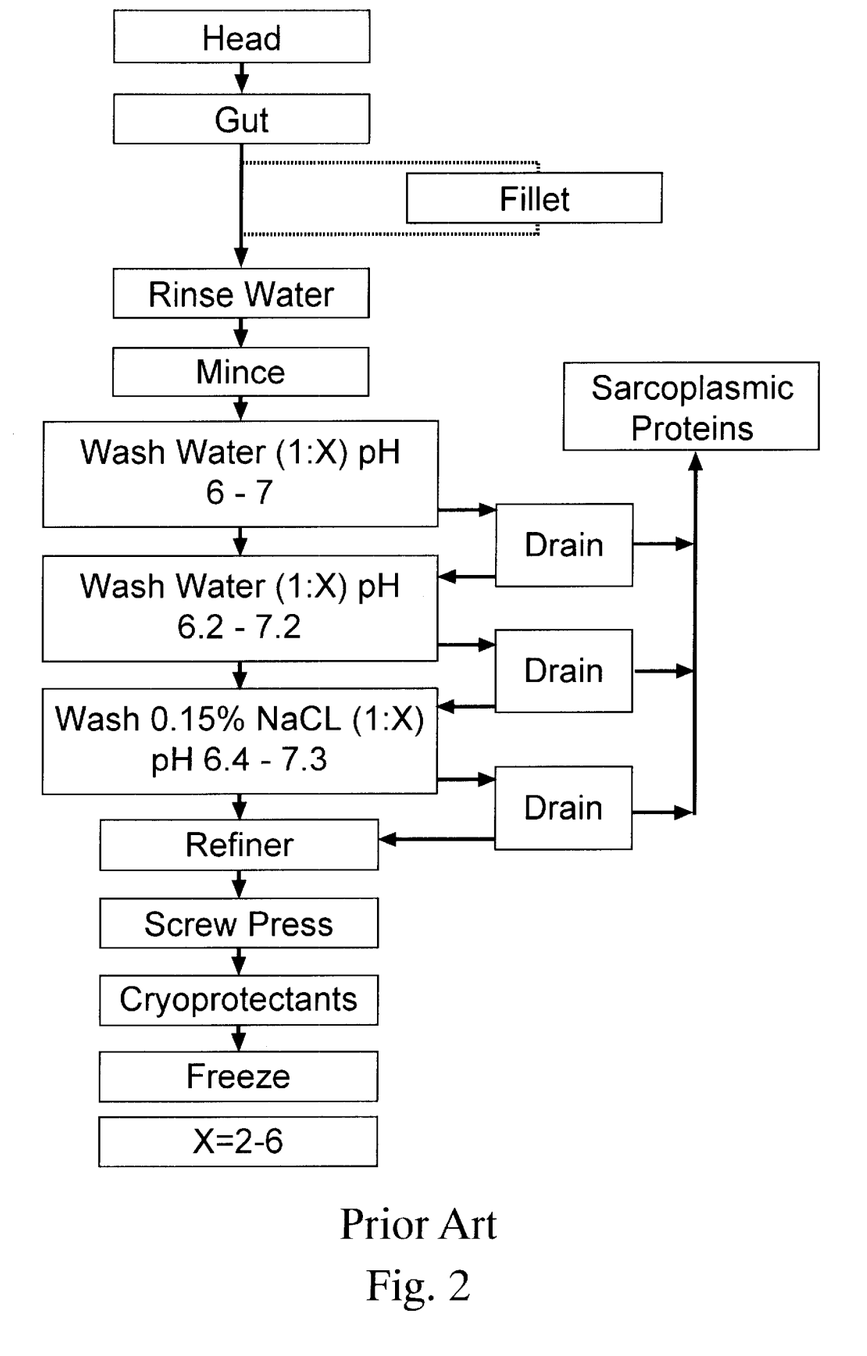
FIG. 2 is a schematic diagram of a conventional process of the prior art.
Figure 3:
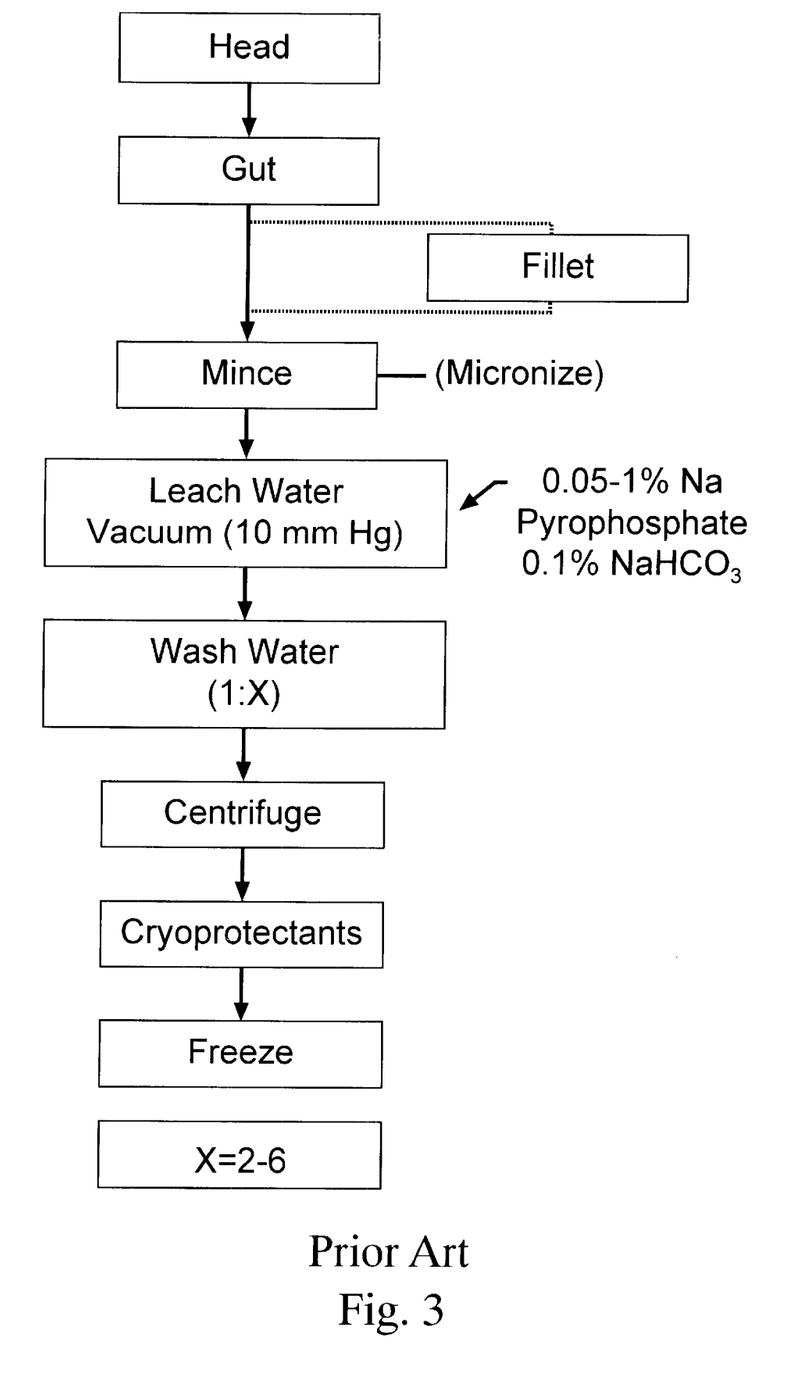
FIG. 3 is a schematic view of an improved conventional process of the prior art.
Figure 4:
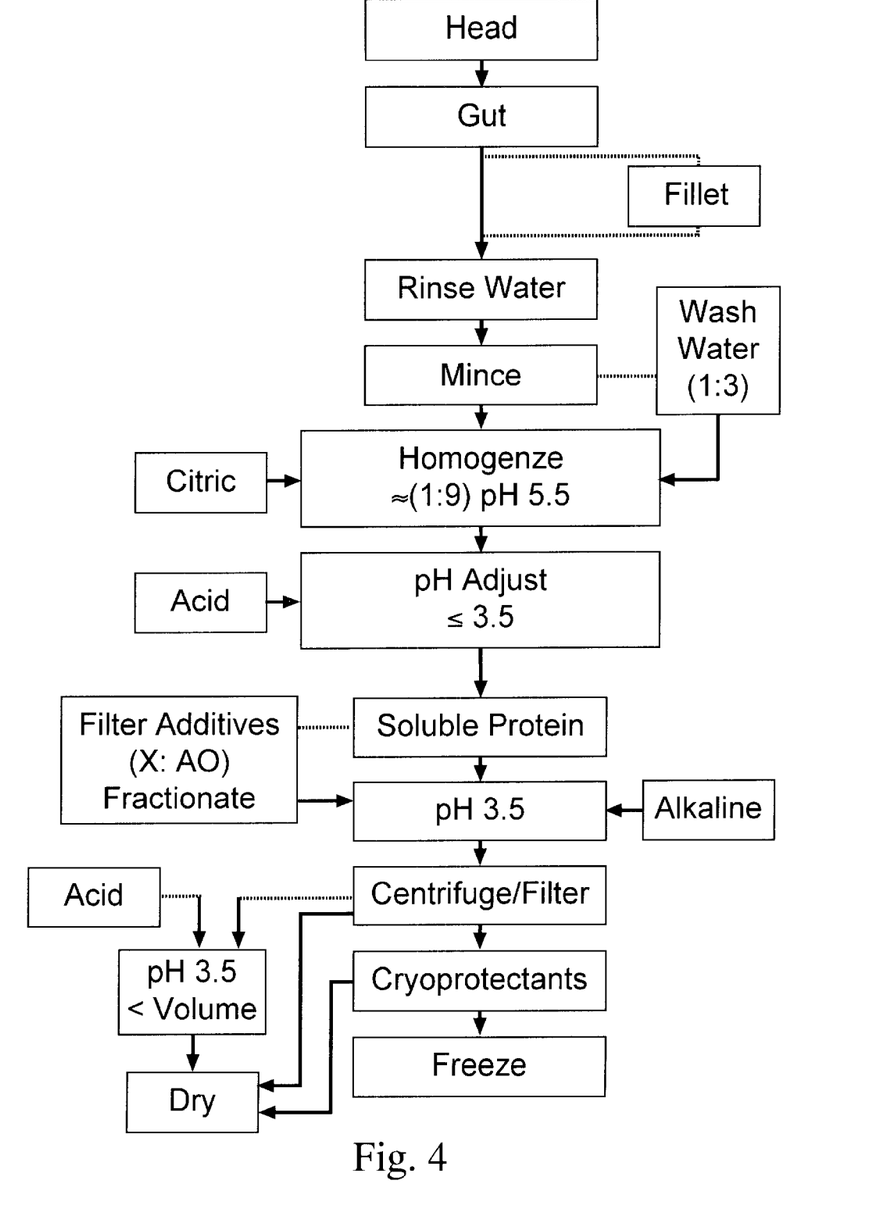
FIG. 4 is a schematic view of a preferred process of this invention.

The following is a description of a process developed to concentrate, and extract proteins from muscle sources in a manner that allows the proteins to retain their functionality (i.e., gelation, emulsification, etc.) throughout the process and into storage. The new acid solubilization/precipitation (ASP) preferred process of this invention is compared to the standard conventional procedure for surimi manufacture, as well as a recent improved conventional process. The improved conventional process was designed to produce a better gel with whiter color and to remove more lipid than was obtained using the conventional method. Flow diagrams for the three processes are shown in FIGS. 2, 3 and 4. In all three procedures the initial steps, heading, gutting, the optional filleting, rinsing and mincing are performed using standard fish processing equipment. It is after these initial steps that the ASP process of this invention substantially changes from the other two processes. The goals of the conventional and improved conventional processes are to keep the proteins under conditions which promote their insolubility, while washing away or removing undesirable soluble components. However, an undesirable sizable loss in protein results. Using the ASP process, conditions are adjusted to promote the solubilization of all the muscle proteins. The conditions are a pH of less than about 3.5 but not too low as to cause destruction to the proteins, and an ionic strength of less than or equal to about 200 mM.

CONVENTIONAL PROCESS

The basic steps of the conventional process are shown in FIG. 2. The amount of times or volumes in the wash steps can vary. Ground or minced fish is washed with refrigerated water (~6° C.) long enough and in large enough volumes to remove undesirable components. Over-washing of the flesh can cause swelling of the proteins, which has been shown to interfere with de-watering and to be deleterious to gel formation. A large proportion of the water soluble components are removed in the first wash with relatively less in subsequent washes. Time spent in the wash, or residence time, also determines washing effectiveness. Between 9–12 minutes has been shown to be an adequate effective residence time per wash. De-watering after each wash is accomplished using a rotary screen. This device is a continuous rolling screen with perforations of approximately 1 mm that allow a partial de-watering. Salt can be added to the final wash to facilitate dewatering. After the final partial de-watering, the washed mince is passed through a refiner. In the refiner, the washed mince is forced against a screen with 0.5 mm perforations under high pressure from a concentric auger. Refining is referred to as the "clean-up" step, where only finely minced muscle is allowed through the perforations. However, separation is not complete and some product is lost in this step. Diverted to a different location is the refiner run-off, which consists of tiny bone and skin fragments and dark muscle, which tends to form in particles larger than 0.5 mm. The refiner is effective at removing unwanted non-edible fragments, but it is not 100% efficient and some particles do get through to the mince. The moisture content at this stage of production is approximately 90%. High moisture allows the refining process to function more effectively. To reduce the moisture content down to the desired 80% refined mince is placed into a screw press. The screw press, like the refiner, pushes the mince against a screen with 0.5 mm perforations using an auger transport, except that the screw press is under higher pressures. Cryoprotectants are added to the de-watered mince to protect the proteins from freeze denaturation and preserve their functionality. A common mixture of cryoprotectants is 4% sucrose, 4% sorbitol and 0.2% sodium tripolyphosphate. In the final step, product is frozen in a plate freezer, which rapidly freezes the product to guard against protein denaturation as does occur during slow freezing.

IMPROVED CONVENTIONAL PROCESS

Three main points of the improved conventional process (FIG. 3) differentiate the process from the conventional process. First, it improves color (lightens) the product by using a "micronization" step, which decreases particle size down to 1–2 microns. This allows very efficient leaching of the undesirable components out of the tissue due to the large surface area. Second, the process also minces or micronizes the tissue under vacuum (10 mm Hg) which has been shown to be effective at reducing oxidation of the lipids. The low vapor pressure caused by the vacuum environment also promotes greater removal of low molecular weight compounds responsible for off or rancid odors. Third, the step in the process which produces the most dramatic effect to the products improvement is that of the addition of sodium bicarbonate (0.1%) and sodium pyrophosphate (0.05–0.1%) to the first wash. The compounds increase the pH of the first wash to approximately 7.2–7.5, which ultimately causes an increase in the gels elasticity and reduces the lipid content to approximately 1%. The process, however, also increases the amount of protein lost during the leaching step. Due to the micronization step, product has to be recovered using centrifugation, which can recover the minute washed tissue particles. The remaining cryoprotection and freezing steps are similar to the conventional process.

ACID SOLUBILIZATION PRECIPITATION (ASP) PROCESS

As mentioned above, a preferred ASP process radically departs from the conventional and improved conventional process following the tissue disruption step. The whole tissue is homogenized in its dilution medium. The homogenization step places muscle tissue (ground or whole) into a solution of 1 mM citric acid, pH 3.0, preferably at a ratio of 1 part tissue to 9 or more parts solution. Lower ratios of tissue solution can be employed depending upon the source of animal tissue in order to avoid gelation. Homogenization equipment that can be used is a Polytron Kinematic homogenizer on speed 76 (1–2 min). The procedure can be scaled up using an Urshel Commitrol Model 1700 or comparable piece of equipment. After homogenization, the pH of the resulting solution is approximately 5.3 to 5.5. At this pH, which is near the isoelectric point of many of the muscle proteins, the up-take of solution by the proteins is at a minimum. This prevents hydration of the proteins and keeps the viscosity low. The pH of the homogenate is then lowered to about pH 3.5 or lower using, but not limited to, hydrochloric acid (HCl). 1 M HCl typically was used, but other mineral or organic acids can perform equally well.

When a 1:9 ratio of tissue: to low pH ($\geq$pH 3.5) solution is used then the resultant protein concentration will be approximately 16 mg/ml for fish and 22 mg/ml for chicken. Viscosities for these solutions can vary from approximately 5 to 30 mPas depending on protein concentration. In virtually all muscle tissue examined using this low pH (and ionic strength) solubilization technique, solubility of the proteins has been between 90–100%.

At the stage in the process when the majority of proteins are in solution, processes such as heating (to destroy possible pathogens or enzymes), additive addition (antioxidants, polymer components, or protein crosslinkers) and/or fractionation of the proteins by size exclusion chromatography or ultrafiltration can be performed. Also, since liquid media are much easier to handle than solids, transporting the product with pumps can be done at this time.

In the next step, raising the pH to a point where the proteins are least soluble and precipitate can be accomplished using numerous types of alkaline compounds. The pH was increased using 1M NaOH for a coarse adjustment and 100 mM NaOH for fine adjustment. Once the solution is adjusted, the proteins can be visualized as white "threads" in the solution. The threads start to appear at pH 3.8 and their concentration steadily increases as the pH increases. At pH values greater than a desired pH, depending upon the source of animal tissue, the solution starts to thicken and takes on a glossy appearance. Samples centrifuged at these higher pHs have large amounts (as high as 40%) of their protein stay in the supernatant and are thus not recovered. Collecting the protein is accomplished by centrifugation; however, the protein can also be obtained by filtration. The moisture content of the sedimenting protein can be somewhat controlled by the centrifugation force. A centrifugation force of 34,000×gravity produced Atlantic cod protein with 78% moisture, whereas, a force of 2575×gravity (table top centrifuge) produced a sample with a moisture content of 84%. Salt or charged polymers also can be used to effect precipitation.

Collected protein can be manufactured into a standard surimi product by the addition of cryoprotectants such as 4% sucrose, 4% sorbitol and 0.5% sodium tripolyphosphate and sufficient base such as sodium carbonate and/or sodium hydroxide to obtain the desired pH from 5.5 to approximately 7.0. The proteins with the cryoprotectants are frozen in a plate freezer, which is standard in the industry.

A protein powder having a pH of about 3.0 is useful in the manufacture of increased protein beverages, such as is found in fruit or sport drinks. To lower the moisture content, it is possible to precipitate the proteins at pH 5.5 and then re-acidify to pH 3.0 using, at most about one-tenth the original volume. This step was done using Atlantic cod proteins, where the protein in solution was increased from 1% to 6.1% prior to drying. This powder can also be used as an emulsifying agent in products such as mayonnaise or salad dressings.

Another product was produced by drying, under vacuum, the precipitated protein from Atlantic cod to which cryoprotectants were added. The powder was hydrated to produce a gel with a strain of 1.1, stress of 26.6 kPa, and a whiteness index of 61.2. Visually the gel contained small particles of tough tissue, which may have been areas where the proteins highly interacted with each other. The incorporation of low or high molecular weight agents, such as negatively charged starches, or sugars can improve the product by interfering with protein-protein interactions. These compounds can be added to the solution at low pH before precipitation.

MAJOR DIFFERENCES BETWEEN PROCESSES

1. Yield Using the conventional process, protein recoveries between 55–65% are commonly found using fish mince as the starting material. Both myofibrillar and sarcoplasmic proteins are removed during the washing steps, with a large majority of these proteins being sarcoplasmic. A large proportion of these proteins come off in the first wash step. The improved conventional process loses additional protein due to the increased pH in the first wash. Yields as low as 31% have been reported. In the ASP process of this invention, higher recoveries of proteins are obtained. Typical protein recoveries using the ASP process are shown in Table 1.

TABLE 1

Protein recoveries for different species using the ASP process

| Muscle type | Protein recovery (%) |
| --- | --- |
| Chicken breast | 84, 92*, 94 |
| Chicken thigh (dark) | 76 |
| Atlantic herring (light) | 88 |
| Atlantic mackerel (light) | 91 |
| Atlantic cod | 92 |
| capelin (headed and gutted) | 63 |

*recovery after the addition of the "soft gel" proteins

2. Gel Values It is generally believed that a strain value of 1.9 is the minimum value needed to be obtained by a gel to be considered as a grade AA gel. The strain value is a measure of cohesiveness or elasticity, thought to be a desired attribute of an excellent gel. Table 2 reports the strain along with the stress values for samples manufactured using the ASP process. For a comparison, a strain value of 1.12 was obtained by using Atlantic mackerel surimi, manufactured using the conventional process on a semi-commercial scale at the NOAA- Mississippi State Univ. seafood pilot plant in Pascagoula, Miss.

TABLE 2

Rheological values for samples manufactured using the ASP process

| Fish (quality) | Strain | Stress (kPa) |
| --- | --- | --- |
| Atlantic cod (v. good) | 2.78 ± 0.91 | 21.98 ± 2.02 |
| Capelin (v. poor) | 2.31 ± 0.22 | 45.04 ± 11.15 |
| Atlantic mackerel light (fair) | 2.61 ± 0.09 | 31.11 ± 3.82 | mean ± standard deviation

3. Color Surimi from Atlantic cod produced using the ASP process developed even whiter gels than surimi with Atlantic cod in the conventional process with a "L" value of 82.3, an "a" value of –0.11, and a "b" value of 2.88. The resultant whiteness index for this sample was 82.1. Values of about 75 or higher are considered excellent.

4. Advantages to Liquid Form The ASP process reduces animal muscle tissue from a solid into a low viscosity fluid with substantially all the proteins in solution. From a processing point of view, this provides a great advantage. Liquids are easier to handle than solids. A major problem in the surimi industry is that bones, skin and blemishes contaminate the end-product. However, as a liquid, proteins in the ASP process can be centrifuged or filtered to assure no contamination enters the final product. The use of the liquid protein solution also simplifies contaminant removal such as metal fragments from equipment. This is a major concern in the production of food. The liquid phase can also be easily temperature controlled in operations such as pasteurization for the elimination of pathogens or rapid cooling. Equipment to move liquids is also much cheaper than equipment needed to move solids. Having the proteins in a liquid form also facilitates fractionating the proteins for either increasing or eliminating specific or groups of proteins. The ASP process also saves processing time because it eliminates the time needed for three or more washes as in the conventional process and can eliminate the refining step. The solubilization step of the proteins takes very little time and can be accomplished in a one-pass system.

Summary

The primary attributes of the process is that it permits the complete solubilization of substantially all of the muscle proteins into a low viscosity fluid. The ASP process can be used to obtain high yields of washed minced fish and to regenerate the functional properties of the muscle proteins from aged or frozen samples. The ASP process allows the proteins obtained to be used in a wide array of food grade products and product enhancers since the products retain the protein functionality.

What is claimed is:

1. A protein containing solid composition recovered from an animal muscle tissue which comprises myofibrillar and sarcplasmic proteins substantially free of myofibrils and sarcomeres and containing membrane proteins of said animal muscle tissue, said proteins capable of being formed into a gel having a strain value of at least 1.1, said protein containing solid composition being formed by the process of:

providing particulate animal muscle tissue free of internal organs, intestines and head of an animal, mixing said particulate animal muscle tissue with an acidic aqueous solution at a pH less than about 3.5 to solubilize substantially all of animal muscle proteins and to open up said myofibrillar proteins of said particulate animal muscle tissue in acidic solution, precipitating said animal muscle proteins containing said membrane proteins in said acidic solution by raising pH or raising ionic strength of said acidic solution to form precipitated animal muscle proteins containing said membrane proteins, and recovering said precipitated animal muscle proteins containing said membrane proteins substantially free of said myofibrils and sarcomeres capable of forming a gel having a strain value of at least 1.1.

2. The protein-containing solid composition formed by the process of claim 1 which includes the further step of freezing said precipitated animal muscle proteins to form a surimi composition capable of forming a gel having a strain value of at least 1.1.

3. The protein-containing solid composition of claim 1 which includes the step of drying said precipitated animal muscle protein to form a powder composition.

4. The composition of any one of claims 1, 2 or 3 which contains at least about 8% up to about 30% by weight sarcoplasmic proteins based upon total weight of protein, said myofibrillar proteins and said sarcoplasmic proteins capable of being formed into said gel.

5. The composition of any one of claims 1, 2 or 3 which contains at least about 10% up to about 30% by weight sarcoplasmic proteins based upon total weight of protein, said myofibrillar proteins and sarcoplasmic proteins capable of being formed into said gel.

6. The composition of any one of claims 1, 2 or 3 which contains at least about 15% up to about 30% by weight sarcoplasmic proteins based upon total weight of protein, said myofibrillar proteins and sarcoplasmic proteins capable of being formed into said gel.

7. The composition of any one of claims 1, 2 or 3 which contains at least about 18% up to about 30% by weight sarcoplasmic proteins based upon total weight of protein, said myofibrillar proteins and sarcoplasmic proteins capable of being formed into said gel.

8. The composition of any one of claims 1, 2 or 3 wherein said animal muscle tissue is fish muscle tissue.

9. The composition of any one of claims 1, 2 or 3 wherein said animal muscle tissue is chicken muscle tissue.

10. The composition of claim 4 wherein said animal muscle tissue is fish muscle tissue.

11. The composition of claim 4 wherein said animal muscle tissue is chicken muscle tissue.

12. The composition of claim 5 wherein said animal muscle tissue is fish muscle tissue.

13. The composition of claim 5 wherein said animal muscle tissue is chicken muscle tissue.

14. The composition of claim 6 wherein said animal muscle tissue is fish muscle tissue.

15. The composition of claim 6 wherein said animal muscle tissue is chicken muscle tissue.

16. The composition of claim 7 wherein said animal muscle tissue is fish muscle tissue.

17. The composition of claim 7 wherein said animal muscle tissue is chicken muscle tissue.

* * * * *

UNITED STATES PATENT AND TRADEMARK OFFICE
CERTIFICATE OF CORRECTION

PATENT NO. : 6,451,975 B1 Page 1 of 1
DATED : September 27, 2002
INVENTOR(S) : Herbert Hultin and Stephen Kelleher It is certified that error appears in the above-identified patent and that said Letters Patent is hereby corrected as shown below:

Column 1,
Line 4, add as the first sentence:

-- This invention was made with government support under Grant NA900AA-D-SG 424 awarded by the U.S. Department of Commerce (NOAA). The government has certain rights in the invention. --

Signed and Sealed this

Twenty-ninth Day of April, 2003

JAMES E. ROGAN
*Director of the United States Patent and Trademark Office*